United States Patent [19]
Miller

[11] Patent Number: 5,020,530
[45] Date of Patent: Jun. 4, 1991

[54] INHALATION THERAPY DEVICE

[76] Inventor: Warren C. Miller, 623 Bay Vista, Seabrook, Tex. 77586

[21] Appl. No.: 519,912

[22] Filed: May 7, 1990

[51] Int. Cl.⁵ .............................................. A61M 16/10
[52] U.S. Cl. ........................... 128/203.28; 128/200.21; 128/205.13
[58] Field of Search ........................ 128/203.28, 203.12, 128/200.14, 200.21, 200.22, 207.14, 205.13, 204.18, 204.25

[56] References Cited
U.S. PATENT DOCUMENTS 3,967,619 7/1976 Story et al. ...................... 128/205.13
4,823,784 4/1989 Bordoni et al. ................ 128/200.16

Primary Examiner—Edgar S. Burr
Assistant Examiner—Stephen R. Funk
Attorney, Agent, or Firm—Ross, Howison, Clapp & Korn

[57] ABSTRACT

An inhalation therapy device has a first conduit joining a nebulizer to a patient breathing port, having a one way check valve. An expandable reservoir for receiving medication from the nebulizer joins the first conduit. A second conduit connected to the first conduit has a filter in a filter housing and a restricted orifice through which both inhalation from, and exhalation to, the atmosphere occurs.

12 Claims, 2 Drawing Sheets

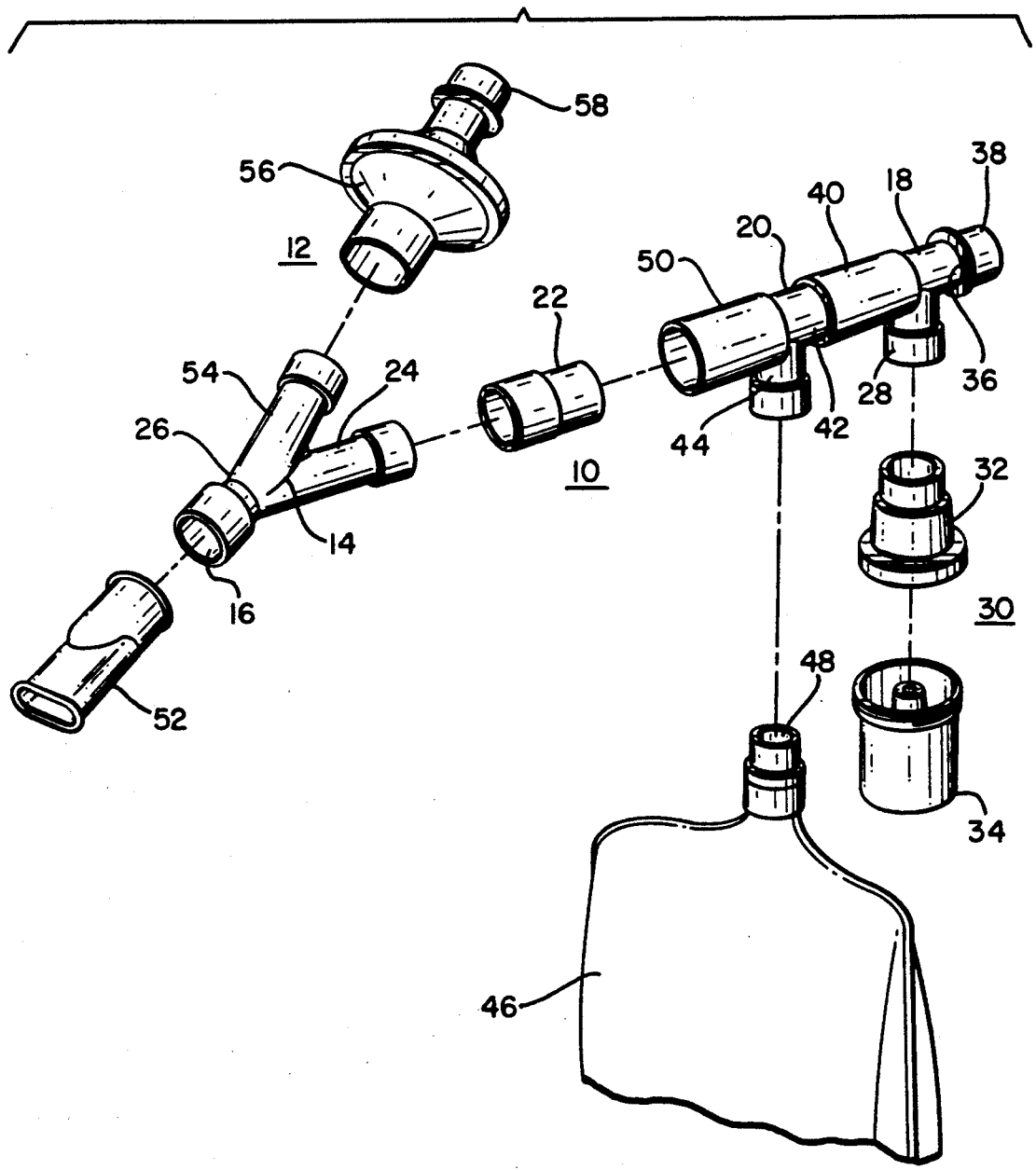

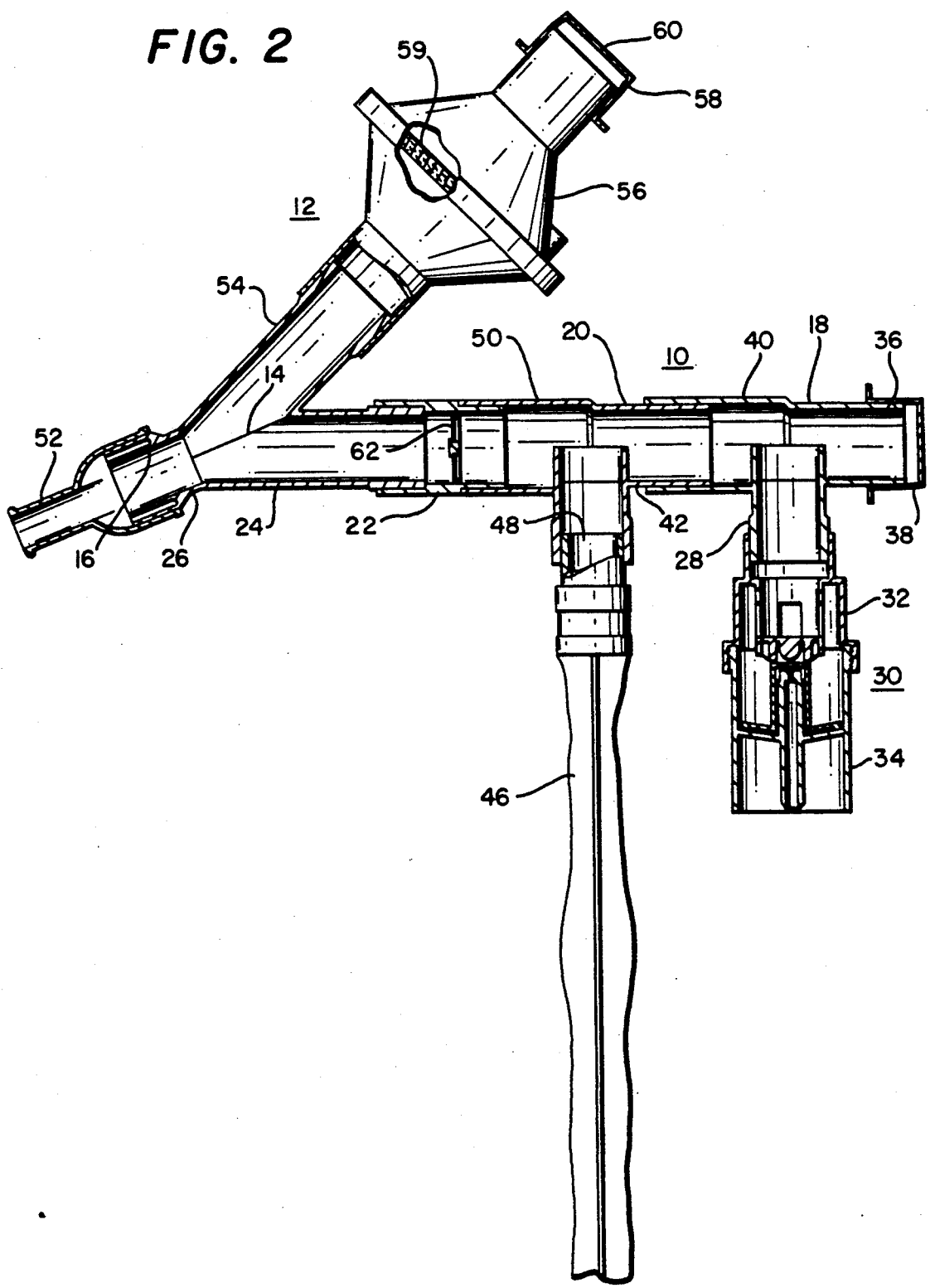

INHALATION THERAPY DEVICE

TECHNICAL FIELD OF THE INVENTION

This invention relates to inhalation therapy, and more particularly to disposable apparatus employing a breathing circuit for delivering a drug in aerosol form to the lungs with improved efficiency.

BACKGROUND OF THE INVENTION

Substantial attention has been directed over many years to the design of disposable devices for producing a mist of medication and delivering it to the airways of a patient under treatment. One important application for such devices is a treatment for pneumocystis carinii pneumonia, a common infection of patients afflicted with acquired immune deficiency syndrome. The delivery of a fine mist of pentamidine isethionate deeply into the lungs of a patient is a recommended therapy for this form of pneumonia.

Devices presently in use for delivery of pentamidine in aerosol form have proven to be relatively inefficient. In a typical 300 mg. dosage treatment, only a minor fraction of the medication actually is deposited in the lungs. Substantial portions are vented to the expiratory filter or otherwise left as unusable residue in the devices. With expensive drugs such as pentamidine, this inefficiency adds substantially to the cost of therapy. The medication cost for a typical dosage of pentamidine to the patient is on the order of $300.

A most widely used device for pentamidine delivery is the Respirgard II marketed by Marquest Medical Products of Inglewood, Colo. The Respirgard II product is substantially similar to the disposable devices illustrated in U.S. Patent No. 4,823,784, particularly the one in FIG. 4. The breathing circuit defined by the Respirgard device and the patent is separated between two distinct legs, one for inhalation and one for exhalation. The aerosol medication from a nebulizer joins the inhalation conduit downstream from an ambient air intake. Check valves are provided in the inhalation conduit on both sides of the nebulizer. During inhalation, the patient draws in air both from the atmosphere and the nebulizer through the inhalation conduit. The exhalation conduit is provided with a check valve and filter to receive all air flow from patient exhalation. The check valve in the exhalation leg prevents any intake of air through that leg during inhalation.

One result from this breathing circuit arrangement is that, if the aerosol medication continues to be produced from the nebulizer during patient exhalation, substantial amounts of medication will be lost to the expiratory filter by being expelled with the exhalent. U.S. Patent No. 4,823,784, in FIG. 1, shows a T provided at the inlet of the nebulizer with a vent port so that the aerosol will only be produced when the patient or a clinician places a finger over the port. Such an arrangement complicates usage, and has not been widely employed.

Moreover, the breathing circuitry of the state of the art device does not inherently encourage the slow deep breathing which is desired for maximum effectiveness in this type of therapy. Patients tend to take rapid and relatively shallow breaths, and unless carefully coached and supervised, generally do not take deep, slow breaths, failing to optimize their treatment. In addition, the devices of the prior art have a tendency to waste substantial amounts of the medication simply by deposition of the medication on the walls of the nebulizer.

SUMMARY OF THE INVENTION

In accordance with this invention, there is provided an inexpensive disposable breathing circuit device which addresses the problems inherent in the prior art. Improved efficiency of delivery of the medication in aerosol form is accomplished by utilization of this invention. In one aspect, the invention contemplates the addition of an expandable reservoir in the breathing circuit downstream from the nebulizer, so that aerosol medication being produced at times when the patient is not inhaling can be stored so that it will be subsequently inhaled and usefully applied to the therapy. Moreover, by closing the leg of the circuit containing the nebulizer so that ambient air does not enter the leg during inhalation, improved breathing patterns are encouraged. Inhalation by the patient in excess of the production of the nebulizer and reservoir bag comes through a restricted orifice on the leg of the breathing circuit which conducts exhalent, so that such leg serves both inhaling and exhaling functions.

In one respect, the inhalation therapy device constructed in accordance with this invention comprises a nebulizer having an inlet adapted to connection to a positive pressure air source, a receptacle for receiving medication in liquid form to be nebulized, and an outlet for dispensing that medication in aerosol form. The nebulizer outlet is connected to a patient breathing port by a first conduit which includes a check valve for permitting flow only in the direction toward the breathing port. An expandable reservoir is provided in communication with the first conduit, upstream from the check valve, to receive medication produced by the nebulizer at times when the patient is not inhaling. A second conduit intersects the first conduit between the check valve and the breathing port, and leads to atmosphere.

In a particular aspect of the invention, the second conduit is provided with a restricted orifice and is free from check valves, so that inhalation at the breathing port in excess of the output of the nebulizer will draw air in from the atmosphere through the second conduit against the resistance provided by the restricted orifice. The first conduit is sealed except for its connection to the nebulizer outlet, patient breathing port, expandable reservoir and second conduit. In one specific form of the invention, the second conduit, used for both inhalation and exhalation is provided with a filter housing having a filter for screening microorganisms or other contaminants from introduction into the atmosphere during exhalation. A restricted orifice in the second conduit serves to promote deep breathing by the patient. Moreover, the filter housing has a significant volume as a dead space to receive exhalent, further encouraging deeper inhalation.

In another aspect of the invention, the interior walls of the nebulizer are coated with a surface active agent for minimizing deposition of liquid medication on the walls of the nebulizer. The coating is one which reduces the surface tension of the nebulizer walls. In a specific form of the invention, the surface active agent coating on the nebulizer walls comprises the combination of an alcohol, glycerin and a soap. In a preferred form, the alcohol is isopropyl alcohol. A preferred soap is an alkanolamine.

BRIEF DESCRIPTION OF THE DRAWINGS

A more complete understanding of the invention may be obtained by reference to the following detailed description when taken in conjunction with the accompanying drawings, wherein:

FIG. 1 is a partially exploded perspective view of an inhalation therapy device constructed in accordance with the present invention; and FIG. 2 is a cross-sectional view of the device of FIG. 1 along its longitudinal axis.

DETAILED DESCRIPTION OF THE INVENTION

An inhalation therapy device constructed in accordance with a preferred embodiment of this invention employs a breathing circuit having a first conduit 10 and a second conduit 12, which intersect at 14 adjacent to a patient breathing port 16. The first conduit 10 is formed by the joinder of t-fitting 18, t-fitting 20, check valve 22 and leg 24 of y-fitting 26. Leg 28 of t-fitting 18 is connected to a conventional aerosol nebulizer 30, including nebulizer cap 32 and nebulizer base 34. Leg 36 of fitting 18 is closed to air passage by sealing cap 38. T-fittings 18 and 20 are joined at their respective legs, 40 and 42. Nebulizer base 34 includes an inlet for receiving pressurized air to atomize the medicine placed in nebulizer 30 and deliver it to first conduit 10.

A leg 44 of fitting 20 is connected to an expandable reservoir 46 which is sealed closed except for its access through port 48 to fitting 20. Reservoir 46 may be formed as a collapsible bag of vinyl or other suitable plastic material. The capacity of reservoir 46 when it is fully expanded, is preferably at least about 1000 milliliters. Leg 50 of fitting 20 is joined with check valve 22, which permits flow only in the direction away from nebulizer 30 towards breathing port 16. Check valve 22 is directly joined to leg 24 of y-fitting 26. The check valve 22 may be of a conventional type employing a flexible disc 62 which is supported on its upstream side at its periphery, so that it closes when pressured from the left as seen in FIG. 2, but permits flow from the right. Disc 62 not only regulates flow, but as in the prior art, screens out excessively large droplets from the aerosol.

It will thus be appreciated that conduit 10 comprises a closed and sealed conduit having only access to the nebulizer 30, expandable reservoir 46, second conduit 12, and breathing port 16. Breathing port 16 of y-fitting 26 may be provided with any suitable interface for patient use in breathing, such as mouthpiece 52. Conduit 12 is formed by leg 54 of y-fitting 26, filter housing 56 and cap 58 with restricted orifice 60. Filter housing 56 is also of conventional design supporting a relatively fine filter 59. The volume of filter housing 56 is significant in improvement of patient breathing patterns, and should be, in a preferred form of the invention, of sufficient size to allow the expiratory circuit 12 to enclose a volume of at least about 65 ml.

All of the structural components which make up the breathing circuit illustrated may be provided from conventional elements available in the industry. The components may be friction fit together to form the device.

The interior surfaces of nebulizer cap 32 and reservoir 46 are specially coated, in a preferred form of the invention, by a surface active agent to reduce wetting of the nebulizer by the medication. Preferably the coating is formed by an alcohol/glycerine emulsion, which is applied by spraying or wiping. A preferred alcohol for the coating is isopropyl alcohol. A preferred soap is an alkanolamine. Cap 58 is provided with a restricted orifice 60 which is sized in accordance with patient lung capacity. The range of suitable orifice diameters is from about 6 mm. to about 10 mm.

In use, the device depicted in FIGS. 1 and 2 accomplishes improved efficiency of medication delivery. Inhalation by the patient is encouraged toward an optimal deep and slow breathing pattern by the restricted orifice 60 and filter housing dead space. Aerosol medication produced by nebulizer 30 is stored in expandable reservoir 46 when not inhaled by the patient. It is thus available for delivery on subsequent inhalation. Waste of medication on the walls of nebulizer 30 is reduced by the surface active agent coating.

Although the preferred embodiment has been described in detail, it should be understood that various changes, substitutions and alterations can be made therein without departing from the spirit and scope of the invention as defined by the appended claims.

I claim:

1. An inhalation therapy device comprising:
   (a) a nebulizer having an inlet adapted for connection to a positive pressure air source, a receptacle for receiving medication in liquid form to be nebulized, and an outlet for continuously dispensing the medication in aerosol form;
   (b) a patient breathing port;
   (c) a first conduit connecting the nebulizer outlet to the breathing port;
   (d) a check valve in the first conduit for permitting flow only in the direction from the nebulizer toward the breathing port.
   (f) a second conduit intersecting the first conduit between the check valve and the breathing port, and leading to atmosphere.

2. The device of claim 1, wherein the second conduit is provided with a restricted orifice, and is free from check valves so that inhalation at the breathing port in excess of the output of the nebulizer and reservoir will draw air in from atmosphere through the second conduit against the resistance provided by the restricted orifice.

3. The device of claim 2, wherein the first conduit is sealed except for its connection to the nebulizer outlet, patient breathing port, expandable reservoir and second conduit.

4. The device of claim 1, wherein the expandable reservoir has an expanded volume of at least about 1000 ml.

5. An inhalation therapy device comprising:
   (a) a nebulizer having an outlet, and an inlet adapted for connection to a positive pressure air flow source;
   (b) a patient breathing port;
   (c) a first conduit connecting the outlet of the nebulizer to the breathing port;
   (d) a check valve in the first conduit for permitting flow only in the direction from the nebulizer to the breathing port;
   (e) an expandable reservoir in communication with the first conduit;
   (f) a second conduit intersecting the first conduit between the check valve and the breathing port and leading to atmosphere;
   (g) a filter housing with filter interposed in the second conduit; and (h) a restricted orifice in the second conduit between the filter housing and atmosphere, adapted to pass air both to and from atmosphere.

6. The device of claim 5, wherein the second conduit encloses a volume of at least about 65 ml.

7. The device of claim 5, further comprising a mouthpiece secured to the breathing port.

8. The device of claim 5, further comprising a coating on the interior walls of the nebulizer of a surface active agent for minimizing wetting of the walls.

9. In an inhalation therapy device including a nebulizer positioned in a breathing circuit for atomizing a liquid medication to be delivered to a patient's lungs, the improvement comprising a coating on the interior walls of the nebulizer comprising a surface active agent for minimizing deposition of the liquid medication on the walls of the nebulizer.

10. The device of claim 9, wherein the surface active agent comprises the combination of an alcohol and a soap.

11. The device of claim 10, wherein the alcohol is isopropyl alcohol.

12. The device of claim 10, wherein the soap is an alkanolamine.

* * * * *

UNITED STATES PATENT AND TRADEMARK OFFICE
CERTIFICATE OF CORRECTION

PATENT NO. : 5,020,530

DATED : JUNE 4, 1991

INVENTOR(S) : WARREN C. MILLER

It is certified that error appears in the above-identified patent and that said Letters Patent is hereby corrected as shown below:

Column 4, line 35, please insert the following:

(e) means for receiving and storing aerosol medication from the outlet of the nebulizer during periods when no air is being taken in by the patient through the patient breathing port, and for delivering such stored medication to the patient upon subsequent inhalation, such means comprising an expandable reservoir in communication with the first conduit upstream from the check valve; and Signed and Sealed this Nineteenth Day of April, 1994

*Attest:*

BRUCE LEHMAN

*Attesting Officer*     *Commissioner of Patents and Trademarks*